United States Patent [19]

McGinity et al.

[11] Patent Number: 5,051,261

[45] Date of Patent: Sep. 24, 1991

[54] METHOD FOR PREPARING A SOLID SUSTAINED RELEASE FORM OF A FUNCTIONALLY ACTIVE COMPOSITION

[75] Inventors: James W. McGinity, Austin, Tex.; Kuei-Tu Chang, Mountain Lakes, N.J.

[73] Assignee: FMC Corporation, Philadelphia, Pa.

[21] Appl. No.: 499,400

[86] PCT No.: PCT US88/04208
§ 371 Date: Apr. 26, 1990
§ 102(e) Date: Apr. 26, 1990

[22] PCT Filed: Nov. 23, 1988

Related U.S. Application Data

[63] Continuation-in-part of Ser. No. 124,705, Nov. 24, 1987, abandoned.

[51] Int. Cl.$^5$ .......................... A61K 3/10; A61K 3/06; A61K 3/07
[52] U.S. Cl. ................................... 424/464; 424/451; 424/489; 424/499; 424/501; 424/78; 424/81
[58] Field of Search ............... 424/464, 468, 489, 499, 424/501, 484, 486–488, 78, 81; 514/964

[56] References Cited

U.S. PATENT DOCUMENTS

| Re. 27,107 | 3/1971 | Levesque | 424/22 |
|---|---|---|---|
| 4,059,686 | 11/1977 | Tanaka et al. | 424/19 |
| 4,166,800 | 9/1979 | Fong | 252/316 |
| 4,181,786 | 1/1980 | Mune et al. | 424/78 |
| 4,226,848 | 10/1980 | Nagai et al. | 424/19 |
| 4,250,163 | 2/1981 | Nagai et al. | 424/14 |
| 4,308,251 | 12/1981 | Dunn et al. | 424/19 |
| 4,353,887 | 10/1982 | Hess et al. | 424/15 |
| 4,357,312 | 11/1982 | Hsieh et al. | 424/15 |
| 4,384,975 | 5/1983 | Fong | 427/213.36 |
| 4,443,497 | 4/1984 | Samejima et al. | 427/213.36 |
| 4,479,911 | 10/1984 | Fong | 264/4.6 |
| 4,499,066 | 2/1985 | Moro et al. | 424/19 |
| 4,547,359 | 10/1985 | Zierenberg et al. | 424/22 |
| 4,647,599 | 3/1987 | Bezzegh et al. | 523/105 |
| 4,652,441 | 3/1987 | Okada et al. | 424/19 |
| 4,659,558 | 4/1987 | Urquhart et al. | 424/470 |
| 4,661,104 | 4/1987 | von Bittera et al. | 424/78 |
| 4,666,702 | 5/1987 | Junginger | 424/497 |
| 4,692,337 | 9/1987 | Ukigaya et al. | 424/469 |
| 4,716,041 | 12/1987 | Kjornaes et al. | 424/468 |
| 4,801,460 | 1/1989 | Goertz et al. | 424/465 |
| 4,880,585 | 11/1989 | Klimesch et al. | 424/486 |
| 4,908,208 | 3/1990 | Lee et al. | 424/409 |

FOREIGN PATENT DOCUMENTS 0241178 10/1987 European Pat. Off. .
2031917 4/1980 United Kingdom .

OTHER PUBLICATIONS

Gennaro, A. R., "Remington's Pharmaceutical Sciences", 17th Ed., Mack Publishing Co., Easton, PA. (1985) pp. 277–279; 1603–1615 and 1650–1654.
Watson, P. D., "Lactic Acid Polymers", Industrial and Engineering Chemistry, 40:8, Aug. 1948, pp. 1393–1397.
Kirk-Othmer, Encyclopedia of Chemical Technology, 3rd. Ed., vol. 17, John Wiley & Sons, N.Y., 1982, pp. 298–307.
FMC Corp.'s "Avicel PH" Bulletin pH (1986).
FMC Corp.'s "Avicel RC/CL" Bulletin RC-16 (1986).
Patent Abstracts of Japan, vol. 4, No. 182 C35.

*Primary Examiner*—Thurman K. Page
*Assistant Examiner*—Edward J. Webman
*Attorney, Agent, or Firm*—R. E. Elden; P. C. Baker

[57] ABSTRACT

The invention is a sustained release dosage or delivery form, such as a tablet, pill, granule or the like capable of providing sustained release of a functionally active ingredient and the method for its manufacture. The invention comprises a matrix of a polymer containing functionally active ingredient and an excipient shaped at or above the glass transition temperature of said polymer into a form such as a granule, tablet or the like. Preferably the excipient is a microcrystalline cellulose.

6 Claims, No Drawings

METHOD FOR PREPARING A SOLID SUSTAINED RELEASE FORM OF A FUNCTIONALLY ACTIVE COMPOSITION

This is a continuation-in-part of copending U.S. application Ser. No. 124,705 filed Nov. 24, 1987 now abandoned.

BACKGROUND OF THE INVENTION

This invention relates to a method for preparing a dosage form, such as a tablet, a bead or the like, with a controlled and delayed release of the active ingredient and the controlled release dosage form made by the process.

It is known to produce solid pharmaceutical or other functionally active preparations which ensure a sustained release of an active ingredient over a long period of time and thus ensure a constant concentration of active ingredient in the body. These delayed release forms make it possible to reduce the number of doses of the drug to be administered daily and thus simplify the treatment plan considerably. Usually delayed release tablets and capsules are provided with a coating which regulates the release of active ingredient.

One disadvantage of relying on coatings for the delayed release property is that any inadvertent puncture of the coating or division of the tablet critically affects the coating integrity or the total surface area of the tablet, that is, some of the barrier coating effectiveness is lost. As a result, the characteristics of the release of active ingredient are significantly altered, so that in many cases, the delayed release tablets no longer have the property of delayed and continuous release of an active ingredient.

In addition, tablets with score lines are known which enable the tablets to be divided into partial doses in order to meet special therapeutic requirements. Divisible tablets of this kind must, in particular, satisfy the requirement of being easy and safe to divide and of ensuring precise dosage, even when broken into fragments.

Microencapsulated formulations do not wholly overcome the problem of controlled release because the film-forming agent frequently forms a continuous phase after a period of time making it impossible to maintain reproducible release rates. U.S. Pat. No. 4,716,041 to Kjornaes et al. teaches a microencapsulated formulation of a first, inner film-forming coating, a second, outer film coating. The coated formulations are subsequently heated to permit the inner film-forming coating to form a continuous phase with uniform diffusion characteristics with time. Such a multiple coating process adds to the expense of a formulation and does not overcome the problem of coating integrity for tablets, caplets and other dosage forms.

Orally administerable pharmaceutical preparations are known in which the active substance is embedded in a polymer or matrix. The matrix slowly dissolves or erodes to release the pharmaceutically active ingredient. The feed formulations of pharmaceutical preparations of this kind are normally produced by dissolving the active ingredient together with a polymer in a solvent, then evaporating the solvent and granulating the solid mixture. Frequently the removal of the solvent and the granulation are carried out in a single operation by spray drying.

Pharmaceutical preparations of this type are intended for the purpose of distributing the active ingredient in a finely dispersed form through the polymer and increasing the surface area of the substance which is to be dissolved, so as to accelerate and not delay the dissolving process.

U.S. Pat. No. 4,547,359 teaches that a divisible polyacrylate-based tablet may be formed of a compressed composition comprising a finely divided polyacrylate material having the active ingredient incorporated therein in molecular dispersion, and conventional tablet excipients. However, the patent teaches it is particularly important to use a specific acrylate polymerized by emulsion polymerization and having a particle size of about 140 nm. Polyacrylates prepared by other methods, such as by solution or block polymerization, are unsuitable for purposes of the invention. In order to ensure a delayed release of the active ingredient, the active ingredient embedded in the polyacrylate material should have diffusion coefficients of $10^{-5}$ to $10^{-7}$ cm$^2$ per hour. However, it is undesirable to restrict the pharmaceutically active compounds to such a narrow range of diffusion coefficients.

U.S. Pat. No. 4,692,337 to Ukigaya et al. teaches that prior art formulations based on a water-insoluble or slightly water soluble matrix have two disadvantages, the weight percentage of the matrix material must be 50% or more of the total weight, and that the rate of release of the medication rapidly decreases with time. Instead, the patent teaches dry mixing 100 parts of the active ingredient, theophylline, with 5 to 200 parts of ethyl cellulose and compressing the mixture into tablets.

Polylactic acid (PLA) is a well-known biologically compatible, insoluble polymeric body employed for the sustained release of pharmaceutical ingredients. U.S. Pat. No. 4,357,312 teaches an implantable matrix suitable for dispensing pharmaceutical ingredients in which the pharmaceutical ingredient is dissolved in a mixture of polylactic acid, solvent and water. Freezing the water creates channels, and subsequent drying removes the solvent and water. The freezing conditions must be carefully controlled to make the release of the pharmaceutical ingredient uniform.

U.S. Pat. No. 4,659,558 discloses bioerodable polymers useful to form coatings including polycarboxylic acids, polyamides, polylactic acid, polyglycolic acid and the like.

U.S. Pat. No. 4,666,702 teaches a drug delivery tablet containing a central core and a coating which is a thermoplastic polymer, optionally polylactic acid, nylon, polyglycolic acid and the like.

U.S. Pat. No. 4,652,441 teaches a microcapsule or bead suitable for controlled release of a water soluble pharmaceutical ingredient including an oil layer thickened with polylactic acid.

DESCRIPTION OF THE INVENTION

The present invention overcomes the disadvantages of the prior art processes. The invention is a method for preparing a sustained release dosage or delivery form comprising blending a dosage amount of a functionally active ingredient, an excipient and a polymer having a glass transition temperature of about 30° C. to about 150°C. into a feed formulation, said polymer being present in sufficient quantity to form a matrix containing the functionally active ingredient, processing at least part of the feed formulation into a shaped form, and maintaining the shaped form at or above the glass transition temperature of the polymer for a sufficient time to provide a dosage form having controlled, sustained release of the functionally active ingredient when the dosage form is administered.

DETAILED DESCRIPTION

Polymers are known to be useful for forming a matrix-type sustained release dosage form. It has unexpectedly been found that a polymer having a glass transition temperature of about 30° C. to about 150° C. when maintained at or above the glass transition temperature in the presence of an excipient and a functionally active ingredient is capable of a controlled, sustained release of the ingredient even when the polymer comprises as little as 5% by weight. A polymer with a glass transition temperature of about 40° C. to about 100° C. is preferred because of thermal stability and to provide a dosage form having controlled sustained release property which does not require refrigeration during shipment or storage in tropic climates.

Although the invention is disclosed in terms of a unitary matrix tablet, the scope of the invention is intended to include any matrix form such as a tablet, bead, microcapsule, densified nonpareil, pill, granule and the like comprised of a functionally active ingredient, an excipient and any polymer or copolymer having a glass transition temperature from about 30° C. to about 150° C. The shaped form may subsequently be reprocessed into other dosage forms. For example, granules or small pills may be processed into capsules, or may be tabletted.

Exemplary polymers or copolymers include low (branched) and high (linear) density polyethylene, polypropylene, poly(propylene/ethylene), polyisobutylene and higher homologs, poly(ethylene/isobutylene), poly(isoprene/isobutylene), ethylene/propylene/diene terpolymers (EPDM), methyl methacrylate polymers or copolymers from acrylic, or methacrylic, hydroxyalkyl acrylic or their methyl, ethyl or lauryl esters; polyacrylonitrile, vinyl acetate homopolymer or copolymers with vinyl stearate, 2-ethylhexyl acrylate or ethyl acrylate, poly (vinyl butyral), poly(vegetable oil acid/ethylene diamine), polyoxymethylene, poly(ethylene oxide), cellulose acetate, acetate butyrate, propionate, acetate propionate, ethylcellulose, poly(ethylene terephthalate) or other polyesters of polyhydric alcohols and dicarboxylic acids, polyether, polyester or polyester/polyamide polyurethanes, poly dimethyl-siloxane or other polysilicones, allyl diglycol carbonate prepolymers and furane resins. Additional polymers include methylcellulose, hydroxypropyl cellulose, hydroxypropylmethylcellulose, hydroxyethylcellulose, cellulose acetate phthalate, polyvinyl acetate phthalate, polyvinyl alcohol, polyvinyl acetate, hydroxypropylmethyl cellulose phthalate, polyhydroxy butyrate, polyhydroxy valerate, polycaprolactone, polylactic acid, polyglycolic acid, polylactic co-glycolic acid, polyglutamic acid, polyanhydrides, polyethylene glycols and polypropylene glycols.

It is desirable for the polymers or copolymers to be either biodegradable or bioerodable, and if to be used to control the release of pharmaceutically active compounds to be pharmaceutically acceptable.

Particularly desirable polymers or copolymers are polyisobutylene, polymers or copolymers of acrylic acid, methacrylic acid, hydroxyalkylacrylic acid, hydroxyalkylmethacrylic acid or their methyl, ethyl or lauryl esters. Other particularly desirable polymers include poly(ethylene oxide), cellulose acetate, cellulose acetate butyrate, cellulose acetate proprionate, ethyl cellulose, polyesters of polyhydric alcohols and dicarboxylic acids, polyethers, cellulose acetate phthalate, dl-polylactic acid, polyglycolic acid, polylactic-polyglycolic copolymers, polycaprolactone, polyhydroxybutyrate, polyhydroxyvalerate and polyethylene glycols.

Any functionally active ingredient may be employed in the present invention, such as a pharmaceutically active ingredient, a flavor, a fragrance, an insecticide, a herbicide, a veterinary product or the like. Particularly desirable are pharmaceutically active ingredients, preferably pharmaceutically active ingredients selected from the group consisting of theophylline, quinidine sulfate, propranolol, chloropheniramine, testosterone and ethenyl estradiol.

Preferred commercial polymers are marketed under the name polyglycolic acid, poly(d,l)lactic acid and poly(d,l)lactic co-glycolic acid (85:15 and 50:50 copolymers) by DuPont and are described in product bulletins "Glycolide S.G." May, 1988 and "Medisorb Bioresorbable Polymers" August, 1988 and both are incorporated herein by reference. The polymers are respectively also called poly(glycolide), poly(d,l-lactide) and poly(D,L-lactide-co-glocolide) in Boehringer Ingelheim's product bulletin "Resorbable Polyesters" which is also incorporated herein by reference. The polymers may be obtained in a range of molecular weights and inherent viscosities.

The polymer, such as dl-polylactic acid (PLA), can be introduced into the feed formulation by any convenient method such as dry mixing, wet granulation method or with a solvent system. In the latter method, the polymer is dissolved in methylene chloride and then blended into the functionally active ingredient and excipient. A lubricant or other additive such as a colorant may be optionally added. The intended scope of the invention includes any polymer having a glass transition temperature above about 30° C. However, polymers having a glass transition temperature of over 150° C. may result in decomposition of the functionally active ingredient or of the excipient. A glass transition temperature of less than 100° C. is preferable for use with many thermally unstable ingredients, such as hydrates.

Heating a dosage form of a pharmaceutically active compound is contrary to the basic practice of pharmacology. One skilled in the art of pharmacology avoids exposure of a dosage form to heat unless absolutely necessary and unless explicitly required, and even then is cooled to minimize the heat to which the active compound is exposed.

Alternatively, the blend can be wet granulated with an aqueous latex dispersion of the polymer which is used as the binding solution. The air dried granulation is then blended with the lubricant and processed into a shaped form.

Drug release is quite rapid for tabletted formulations made by either of these procedures with polylactic acid as the polymer. In less than thirty minutes the drug is fully released into the dissolution medium. As the level of polymer is increased in the formulation from zero percent, no significant retardation of release is achieved.

When no polymer is present in the tablet the tablet hardness decreases as the time of heating increases. On the other hand, the hardness increases with tablets containing polymer as the time of heating increases. The hardness continuously increases with tablets containing at least 15% polymer. With tablets containing 5% to 10% polymer the hardness increases to a plateau. For the purpose of this invention all percentages are expressed as weight percent. Any quantity of polymer may be employed which is sufficient to form a matrix containing the functionally active ingredient, desirably 1% to 90% polymer is sufficient, preferably 5% to 50% polymer. As used herein the term "maintaining the shaped form at or above the glass transition temperature" is intended to include heating by any conventional means prior to administering but does not include thermal effects from compression alone.

Any convenient excipient may be employed in the feed formulation. The excipient may be employed for a single function such as a diluent, a binder, a lubricant, a disintegrant, an adsorbent, or for a combination of functions. Common excipients such as lactose, dicalcium phosphate, calcium sulfate, sugars, microcrystalline cellulose, gums, methylcellulose, starch, polyvinylpyrrolidone, clay and the like may be selected by one skilled in the art to provide their usual contribution to the dosage form. The excipient may be employed in an amount varying from 1% to about 90% by weight.

Particularly desirable excipients are marketed under the tradename of Avicel brand microcrystalline cellulose by FMC Corporation. Microcrystalline cellulose is suitable for use as a binder, a diluent and as a disintegrant. The Avicel PH grades of microcrystalline cellulose are preferred for use in compression shaping. The product is porous which permits the microcrystalline cellulose to absorb a liquid ingredient while remaining a free-flowing powder suitable to serve as a feed formulation for compression. Microcrystalline cellulose also provides an intermediate disintegration rate between the rapid disintegration rate of soluble excipients and the very slow disintegration rate of insoluble excipients such as calcium sulfate.

A polymer, such as polylactic acid, is brittle below its glass transition temperature. The glass transition temperature ("Tg") or second order transition temperature is the temperature at which a polymer changes from a brittle material (glassy state) to a rubbery material. The glass transition temperatures of polymers vary with molecular weight. The glass transition, unlike a true thermodynamic transition, takes place over a temperature range of several degrees and is dependent upon the experimental method and the time scale used for its determination. The glass transition temperature can also vary with the additives employed such as plasticizers, lubricants and the like. Below the transition, the majority of the polymer chains have a fixed configuration and little translation or rotation of chains takes place. Methods used to determine the glass transition temperature and the reported values for a large number of polymers are available in standard references employed by those skilled in the art. For the purpose of this invention the glass transition temperature shall include a temperature below the melting point of a polymer at which the polymer ceases to be a brittle, glassy or crystalline solid and becomes rubbery or begins to flow.

Shaped forms of PLA, a functionally active ingredient and an excipient which have been processed into shaped forms and heated but not heated to the glass transition temperature are usually erratic in their rate of dissolution. Further, the hardness of the shaped forms decreases on heating below the glass transition temperature. However, when heated to or above their glass transition temperature the shaped forms form a matrix. They become consistent in their rate of dissolution and their hardness increases. Further, the rate of dissolution decreases with an increase of concentration of PLA and with the length of time the shaped forms are held at or above the glass transition temperature.

EXAMPLES

The following examples will explain to one skilled in the art the best mode of practicing the invention.

EXAMPLE 1

FEED FORMULATION PROCEDURES

Feed formulations were prepared containing 0%, 5%, 10% and 15% PLA. The functionally active ingredient employed was theophylline and the excipient employed was Avicel PH 101 brand microcrystalline cellulose. 0.5% magnesium stearate was added as a lubricant. Dosage units of 300 mg containing 75 mg theophylline were compressed in a tablet press from a feed formulation containing as follows: 25% theophylline, 74.5% excipient and 0.5% lubricant (0% PLA); 25% theophylline, 69.5% excipient, 0.5% lubricant and 5% PLA; 25% theophylline, 64.5% excipient, 0.5% lubricant and 10% PLA; and 25% theophylline, 59.5% excipient, 0.5% lubricant and 15% PLA.

Although the invention is exemplified in terms of theophylline as the functionally active ingredient, microcrystalline cellulose as the excipient and magnesium stearate as the lubricant, it will be clear to one skilled in the art that any suitable functionally active ingredient, excipient or lubricant may be employed. A dosage amount of a functionally active ingredient can vary over a wide range depending on activity and time of sustained release. Generally 5% to about 50% of the functionally active ingredient will be contained in the matrix.

The feed formulations were prepared by two methods, dissolving the PLA in methylene chloride and adding the solution to the blend of the pharmaceutical ingredient and excipient (the "Organic" method), or by incorporating the PLA as an aqueous latex dispersion (the "Latex" method). The aqueous latices were prepared by emulsion of the organic solution of the polymer with a Gaulin brand laboratory homogenizer. Subsequently, the organic solvent was removed by evaporation. After air drying of the granules a lubricant was added to the feed formulation and 300 mg tablets were formed by direct compression to about 5.5 kg. to 6 kg. The PLA had a glass transition temperature of 55° C. to 57° C.

The hardness, friability and dissolution rates (U.S.P. Method II) of tablets were determined. The hardness and friability results are presented as Tables IA and IB. The dissolution data are presented as Runs 2A to 6C. The numbers to the right of the decimal point indicate a different level of the variable under study in that series with O indicating a control.

Run 1A: The percentage change of hardness on heating up to 24 hours at 60° C. is presented as Table IA for tablets prepared by the Organic method.

Run 1B: The friability of tablets prepared by the Organic method is presented as Table IB as a function of PLA content and time of heating.

Dissolution Runs—Table II.

Run 2A: The rate of dissolution of theophylline is compared for 15% PLA tablets prepared by the solvent method heated for up to 12 hours at 40° C., less than the glass transition temperature.

Run 2B: The rate of dissolution of theophylline is compared for 15% PLA tablets prepared by the solvent method heated for up to 12 hours at 60° C., slightly above the glass transition temperature.

Run 2C: The rate of dissolution of theophylline is compared for 15% PLA tablets prepared by the solvent method heated for up to 24 hours at 60° C., slightly above the glass transition temperature.

Run 3A: The rate of dissolution of theophylline is compared for 5% PLA tablets prepared by the solvent method and heated at 60° C. for up to 24 hours.

Run 3B: The rate of dissolution of theophylline is compared for 5% PLA tablets prepared by the solvent method and heated at 60° C. for up to 12 hours.

Run 4: The rate of dissolution of theophylline from 10% PLA tablets prepared by the Organic method and by the Aqueous Latex method are compared after heating at 60° C. for 1 and 12 hours.

Run 5A: Rates of dissolution of theophylline are compared for tablets (Aqueous Latex method) containing 5%, 10% and 15% PLA and heated for 1 hour at 60° C.

Run 5B: Rates of dissolution of theophylline are compared for tablets (Aqueous Latex method) containing 5%, 10% and 15% PLA and heated 6 hours at 60° C.

Run 6A, 6B and 6C: Rates of dissolution of theophylline are compared for tablets containing 5%, 10% and 15% PLA after heating to 60° C. for up to 24 hours.

From the above data it is clear that the rate of dissolution of a pharmaceutically active ingredient can be controlled by the quantity of polylactic acid or other polymer incorporated into the feed formulation, the method of incorporation, and the time the tablets are maintained at or above the glass transition temperature.

EXAMPLE 2

The influence of thermal treatment was determined on the dissolution properties of drugs from tablets containing various biodegradable polymers. Unless specified otherwise, tablets were prepared from formulation typically containing 25% of a functionally active ingredient, 60% Avicel PH 101 microcrystalline cellulose and 15% polymer. No lubricant was employed.

The functionally active ingredient was mixed with the microcrystalline cellulose for 5 minutes. Granules were prepared by dissolving the polymer in methylene chloride to distribute the polymer homogeneously throughout the matrix. The granules were air dried at 25° C. overnight and tablets were compressed to a weight of 500 mg with a Carver laboratory press at 750 kg pressure. Heat treated tablets were heated at 60° C. for 24 hours. Polymers employed were:

Poly-(dl-Lactide) High MW (UT), Tg 35° C.–40° C., [PLA-HMV]; Poly-(dl-Lactide) Low MW, Tg 40° C.–45° C., [PLA-LMW]; Poly-(l-Lactide), Tg 55° C.–60° C., [L-PLA]; Polycaprolactone 300, mp 60° C.–62° C., [PCL-300]; Polycaprolactone 700, mp 60° C.–62° C., [PCL-700]. The abbreviations to be used herein for the polymers appear in square brackets.

Functionally active ingredients employed were:
Theophylline,
Chlorpheniramine Maleate,
Propanolol Hydrochloride, and
Quinidine Sulfate.

Rate of dissolution of matrix tablets with and without heat treatment were compared according to the method of Example 1. Results are presented as Table III.

Runs 1 and 7 show the rate of dissolution is not a function of the polymer alone, but that the excipient and/or functionally active ingredient also is a factor in controlling the rate of dissolution.

Run 8 is surprising in that the optically active polymer appears ineffective with the same formulation of ingredients that is effective with the racemic polymer. This run indicates that the effect of thermal treatment is unexpected.

EXAMPLE 3

Tablets were prepared as before containing 25% theophylline, 60% Avicel PH 101 brand microcrystalline cellulose and 15% polymer. The polymers were, Run 1, DuPont Medisorb 5050 brand of a 50:50 Poly(D,L)lactic co-glycolic acid polymer, [PLA:PGA], Tg 60° C.–65° C.; Run 2, polyethylene glycol mw 20,000, [PEG 20M]; and Run 3, Ritt Chemical polyisobutylene, [P1B], pour point 112.5° C. The percent theophylline released with time (hours) was: Run 1, no heat treatment; 10%, 0.7 hour; 17%, 1.3 hours; 25%, 2 hours; 39%, 4 hours; 49%, 6 hours and 71%, 12 hours. Run 1, heated 24 hours at 67° C.; 10%, 0.7 hour; 18%, 1.3 hours; 32%, 2 hours; 39%, 4 hours; 47%, 6 hours; and 60%, 12 hours.

Run 2, no heat treatment; 10%, 0.5 hour; 17%, 1 hour, 29%, 2 hours; 88%, 4 hours; and 100%, 6 hours. Run 2, heated 59° C., 24 hours; 10%, 0.5 hour; 19%, 1 hour, 39%, 2 hours; 73%, 4 hours; and 94%, 6 hours. Here the PEG tablets heat treated 24 hours at 59° C. are outstanding in that their rate of release of theophylline is a straight line function of time.

Run 3, no heat treatment 50%, 0.5 hour; 77%, 1 hour; 98%, 2 hours; and 100%, 4 hours.

Run 3, heated 60° C., 24 hours; 79%, 0.5 hour, 92%, 1 hour; 96%, 2 hours; and 97%, 4 hours. Here the rate of release is initially greater with heat treatment but slows sufficiently so that the functionally active ingredient is still being released after the non-heat treated tablet is exhausted.

TABLE IA

INFLUENCE OF 60° C. HEAT ON HARDNESS PLA TABLET

| Hours at 60° C. | % of Initial Hardness | | | |
|---|---|---|---|---|
| | 0% PLA | 5% PLA | 10% PLA | 15% PLA |
| 0 | 100 | 100 | 100 | 100 |
| 1 | 93 | 104 | 100 | 103 |
| 3 | 94 | 104 | NA | 107 |
| 6 | 90 | 103 | 107 | NA |
| 12 | 85 | 104 | 107 | 108 |
| 24 | 87 | 104 | 105 | 110 |

TABLE IB

INFLUENCE OF 60° C. HEAT ON FRIABILITY PLA TABLET

| Hours at 60° C. | % Loss of Friability | | | |
|---|---|---|---|---|
| | 0% PLA | 5% PLA | 10% PLA | 15% PLA |
| 1 | 0.10 | 0.09 | 0.05 | 0.04 |
| 3 | 0.13 | 0.08 | NA | 0.03 |
| 6 | 0.12 | NA | 0.05 | 0.04 |
| 12 | 0.13 | 0.06 | 0.04 | 0.03 |
| 24 | 0.12 | 0.06 | 0.04 | 0.02 |

TABLE II

RELEASE RATE OF TABLETS CONTAINING 25% THEOPHYLLINE

| Run | % PLA Polymer | Heat Treated | Percent Dissolved In | | | | | | | |
|---|---|---|---|---|---|---|---|---|---|---|
| | | | % 0.5 hr. | % 1 hr. | % 2 hr. | % 3 hr. | % 6 hr. | % 12 hr. | % 24 hr. | % 48 hr. |
| 2A.0 | 15% | None | 98 | 100 | 100 | 100 | 100 | 100 | — | — |
| 2A.1 | 15% | 1 hr. 40° C. | 28 | 39 | 52 | — | 65 | 80 | — | — |
| 2A.2 | 15% | 6 hr. 40° C. | 25 | 32 | 42 | — | 62 | 80 | — | — |
| 2A.3 | 15% | 24 hr. 40° C. | 24 | 30 | 40 | — | 61 | 78 | — | — |
| 2B.0 | 15% | None | 98 | 100 | 100 | 100 | 100 | 100 | — | — |
| 2B.1 | 15% | 1 hr. 60° C. | 22 | 31 | 40 | 50 | 63 | 80 | — | — |
| 2B.2 | 15% | 6 hr. 60° C. | 18 | 26 | 35 | NA | 51 | 66 | — | — |
| 2B.3 | 15% | 24 hr. 60° C. | 16 | 23 | 33 | NA | 50 | 64 | — | — |
| 2C.0 | 15% | None | 98 | 100 | 100 | 100 | 100 | — | — | — |
| 2C.1 | 15% | 1 hr. 60° C. | 22 | 30 | 40 | 45 | 64 | 82 | 95 | — |
| 2C.2 | 15% | 6 hr. 60° C. | 18 | 26 | 35 | — | 52 | 64 | 88 | — |
| 2C.3 | 15% | 24 hr. 60° C. | 16 | 23 | 33 | — | 50 | 63 | 79 | — |
| 3A.0 | 5% | None | NA | 98 | 100 | 100 | 100 | 100 | — | — |
| 3A.1 | 5% | 1 hr. 60° C. | — | 27 | 45 | 59 | 81 | 86 | 99 | — |
| 3A.2 | 5% | 12 hr. 60° C. | — | 26 | 44 | 58 | 80 | 85 | 98 | — |
| 3A.3 | 5% | 24 hr. 60° C. | — | 26 | 43 | 58 | 80 | 84 | 99 | — |
| 3B.0 | 5% | None | 98 | 100 | 100 | 100 | 100 | 100 | — | — |
| 3B.1 | 5% | 1 hr. 60° C. | 33 | 50 | 59 | 79 | 82 | 93 | — | — |
| 3B.2 | 5% | 12 hr. 60° C. | 32 | 44 | 58 | 79 | 80 | 93 | — | — |
| 3B.3 | 5% | 24 hr. 60° C. | 31 | — | — | 78 | 80 | 88 | — | — |
| 4L.1 | 10% | 1 hr. 60° C. | 21 | — | 74 | — | — | 92 | — | — |
| 4L.2 | 10% | 12 hr. 60° C. | 20 | 25 | 58 | — | — | 91 | — | — |
| 4O.1 | 10% | 1 hr. 60° C. | 20 | 25 | 45 | — | — | 80 | — | — |
| 4O.2 | 10% | 12 hr. 60° C. | 19 | 24 | — | — | — | 68 | — | — |
| 5A.1 | 5% | 1 hr. 60° C. | — | 58 | 85 | 86 | — | 100 | 100 | 100 |
| 5A.2 | 10% | 1 hr. 60° C. | — | 22 | 43 | 67 | — | 75 | 100 | 100 |
| 5A.3 | 15% | 1 hr. 60° C. | — | 0 | 18 | 20 | — | 26 | 68 | 76 |
| 5B.1 | 5% | 6 hr. 60° C. | 24 | — | 46* | 80 | — | 85 | 84 | — |
| 5B.2 | 10% | 6 hr. 60° C. | 20 | — | 38* | 55 | — | 85 | 85 | — |
| 5B.3 | 15% | 6 hr. 60° C. | 9 | — | 21* | 25 | — | 61 | 78 | — |
| 6A.1 | 5% | 1 hr. 60° C. | 58 | — | 90* | 91 | — | 100 | — | — |
| 6A.2 | 5% | 6 hr. 60° C. | 24 | — | 52* | 80 | — | 92 | — | — |
| 6A.3 | 5% | 12 hr. 60° C. | 23 | — | 40* | 63 | — | 92 | — | — |
| 6A.4 | 5% | 24 hr. 60° C. | 22 | — | 40* | 53 | — | 88 | — | — |
| 6B.1 | 10% | 1 hr. 60° C. | — | 21 | 46* | 73 | — | 93 | — | — |
| 6B.2 | 10% | 6 hr. 60° C. | — | 18 | 37* | 52 | — | 91 | — | — |
| 6B.3 | 10% | 24 hr. 60° C. | — | 16 | 31* | 43 | — | 81 | — | — |
| 6C.1 | 15% | 1 hr. 60° C. | 10 | — | — | 32 | — | 69 | 82 | 98 |
| 6C.2 | 15% | 6 hr. 60° C. | 10 | — | — | 32 | — | 68 | 82 | 98 |
| 6C.3 | 15% | 12 hr. 60° C. | 10 | — | — | 32 | — | 68 | 82 | 97 |
| 6C.4 | 15% | 24 hr. 60° C. | 10 | — | — | 32 | — | 63 | 82 | 98 |

*1½ hour

TABLE III

EFFECT OF HEAT TREATMENT ON RATE OF DISSOLUTION OF FUNCTIONALLY ACTIVE INGREDIENTS (FIA) FROM POLYMERS

| Run | Polymer | FAI | Heat Treated | Percent Dissolved In | | | | | |
|---|---|---|---|---|---|---|---|---|---|
| | | | | % 0.5 hr. | % 1 hr. | % 2 hr. | % 4 hr. | % 6 hr. | % 14 hr. |
| 1 | PLA(LMW) | Theophylline | N | 85 | 98 | 103 | 104 | — | — |
| | | | Y | 52 | 85 | 100 | 105 | — | — |
| 2 | PLA(300) | Theophylline | N | 42 | 60 | 81 | 96 | 102 | 104 |
| | | | Y | 20 | 32 | 47 | 63 | 73 | 92 |
| 3 | PCL(700) | Theophylline | N | 15 | 21 | 32 | 43 | 53 | 73 |
| | | | Y | 8 | 13 | 19 | 27 | 33 | 44 |
| 4 | PLA(HMW) | Chlorpheniramine | N | 25 | 42 | 66 | 91 | 100 | 105 |
| | | | Y | 19 | 28 | 47 | 68 | 88 | 104 |
| 5 | PLA(HMW) | Quinidine Sulfate | N | 15 | 25 | 37 | 54 | 66 | 87 |
| | | | Y | 11 | 16 | 25 | 36 | 48 | 64 |
| 6 | PLA(HMW) | Propanolol | N | 43 | 59 | 79 | 98 | 101 | |
| | | | Y | 26 | 39 | 58 | 77 | 90 | |
| 7 | PLA(LMW) | 60% Theophylline* | N | 42 | 66 | 93 | 100 | 102 | 103 |
| | | | Y | 21 | 42 | 74 | 97 | 101 | 103 |
| 8 | LPLA | Theophylline | N | 86 | 99 | 100 | 100 | | |
| | | | Y | 86 | 98 | 100 | 100 | | |

*60% Theophylline, 25% excipient, 15% polymer

We claim:

1. A method for preparing a sustained release dosage form comprising blending into a feed formulation a dosage amount of a functionally active ingredient, an excipient and a polymer or copolymer having a glass transition temperature of about 30° C. to about 150° C., said polymer being present in sufficient quantity to provide from 5% to 50% polymer or copolymer, 1% to 90% excipient, and from 5% to 90% of the functionally active ingredient in the dosage form, processing at least part of the feed formulation into a shaped form and maintaining the shaped form at or above the glass transition temperature of the polymer for from 1 to 12 hours to provide a dosage form having controlled, sustained release of the functionally active ingredient when the dosage form is administered.

2. A method for preparing a sustained release dosage form comprising blending into a feed formulation a dosage amount of a functionally active ingredient, an excipient and a polymer having a glass transition temperature of 30° C. to 150° C. selected from the group consisting of polyisobutylene, polymers and copolymers of acrylic acid, methacrylic acid, hydroxyalkylacrylic acid, hydroxyalkylmethacrylic acid and their methyl, ethyl and lauryl esters, poly(ethylene oxide), cellulose acetate, cellulose acetate butyrate, cellulose acetate proprionate, ethyl cellulose, polyesters of polyhydric alcohols and dicarboxylic acids, polyethers, cellulose acetate phthalate, dl-polylactic acid, polyglycolic acid, polylactic-polyglycolic copolymers, polycaprolactone, polhydroxybutyrate, polyhydroxyvalerate and polyethylene glycols, mixtures and copolymers thereof to provide from 5% to 50% polymer or copolymer, 1% to 90% excipient and 5% to 90% of the functionally active ingredient processing at least part of the feed formulation into a shaped form characterized by maintaining the shaped form at or above the glass transition temperature of the polymer for from 1 to 12 hours to provide a dosage form having controlled, sustained release of the functionally active ingredient when the dosage form is administered in the dosage form.

3. The sustained release dosage form of claim 1 or 2 characterized in that the polymer or copolymer has a glass transition temperature of 40° C. to 100° C.

4. The sustained release dosage form of claims 1 or 2 characterized in that the excipient is selected from the group consisting of lactose, dicalcium phosphate, calcium sulfate, sugar, microcrystalline cellulose, gums, methylcellulose, starch, polyvinylpyrrolidone and clay.

5. The sustained release dosage form of claim 4 characterized in that the form is a tablet, bead, microcapsule, pill or a granule.

6. The sustained release dosage form of claim 4 characterized in that the pharmaceutically active ingredient is selected from the group consisting of theophylline, quinidine sulfate, propranolol, chlorpheniramine, testosterone and ethenyl estradiol.

* * * * *